US005474931A

United States Patent [19]
DiSorbo et al.

[11] Patent Number: 5,474,931
[45] Date of Patent: Dec. 12, 1995

[54] MEDIA CONCENTRATE TECHNOLOGY

[75] Inventors: Dennis M. DiSorbo, Buffalo; David W. Jayme, Grand Island, both of N.Y.

[73] Assignee: Life Technologies, Inc., Gaithersburg, Md.

[21] Appl. No.: 124,508

[22] Filed: Sep. 21, 1993

Related U.S. Application Data

[63] Continuation of Ser. No. 716,264, Jun. 17, 1991, abandoned.
[51] Int. Cl.$^6$ ............................... C12N 5/00; C12N 1/04
[52] U.S. Cl. ................... 435/240.31; 435/240.2; 435/240.3; 435/244; 252/380; 252/397; 252/401
[58] Field of Search .................... 435/240.2, 240.3, 435/240.31, 240.54, 244; 252/380, 397, 401

[56] References Cited

U.S. PATENT DOCUMENTS 4,879,222  11/1989  Alderman et al. ..................... 435/68

FOREIGN PATENT DOCUMENTS 170550    7/1994  New Zealand.
WO87/00195 1/1987  WIPO.

OTHER PUBLICATIONS

Sigma cell culture reagents 1991 catalogue/price list (OPI–Sep. 25, 1990) pp. 249–251, 279–282.
Ham PNAS. vol. 53 pp. 288–293 (1965).
Terari, et al. J. Inorg. Nucl. Chem. vol. 35 No. 7 pp. 2441–2446 (1973).
Bray et al., "The Enzymic Hydrolysis of Glutamine and its Spontaneous Decomposition in Buffer Solutions", *Biochem. J.* 44:625–627 (1949).
Griffin et al., "Kinetics of Phototoxicity of Fischer's Medium for L5178Y", *Cancer Research* 41:2241–2248 (1981).
Ham, R. G., "Clonal Growth of Mammalian Cells in a Chemically Defined Synthetic Medium", *Proc. Natl. Acad. Sci. USA* 53:288–293 (1965).
Lidgate et al., "Using a Microfluidizer to Manufacture Parenteral Emulsions", *BioPharm*:28–31 (1989).
Masson, G., "Advanced Techniques for Preparation and Characterization of Small Unilamellar Vesicles", *Food Microstructure* 8:11–14 (1989).
Ozturk and Palsson, "Chemical Decomposition of Glutamine in Cell Culture Media, Effect of Media Type pH and Serum Concentration", *Biotechnol. Prog.* 6(2):121–128 (1990).
Tewari et al., "Formation and Stabilities of Bivalent Metal Ion Chelates of L–Glutamine", Chemical Abstracts 79 (16):373, Abstract No. 97604s (1973) and *J. Inorg. Nucl. Chem.* 35(7):2441–2446 (1973).
Tritsch and Moore, "Spontaneous Decomposition of Glutamine in Cell Culture Media", *Experimental Cell Research* 28:360–364 (1962).
Wang and Nixon, "Identification of Hydrogen Peroxide as a Photoproduct Toxic to Human Cells in Tissue–Culture Medium Irradiated with Daylight Florescent Light", *In Vitro 14(8):715–722 (1978)*.
Waymouth, C., Methods for Preparation of Media, Supplements, and Substrata for Serum–Free Animal Cell Culture, ed. Alan R. Liss, Inc., N.Y., pp. 23–68 (1984).
Bray et al., *Biochem. J.* 44:625–627 (1949).
Tritsch et al., *Experimental Cell Research* 28:360–364 (1962).
Wang et al., *In Vitro* 14(8):715–722 (1978).
Ozturk et al., *Biotechnol. Prog.* 6:121–128 (1990).
Griffin et al., *Cancer Research* 41:2241–2248 (1981).
Ham, R. G., *Proc. N.A.S.* 53:288–293 (1965).
Waymouth, C., Methods for Preparation of Media, Suppl., and Substrata for Serum–Free Animal Cell Culture, pp. 23–68 (1984).
Lidgate et al., *BioPharm* pp. 28–31 (1989).
Masson, G., *Food Microstructure* 8:11–14 (1989).

*Primary Examiner*—Michael G. Wityshyn
*Assistant Examiner*—Jane Willimas
*Attorney, Agent, or Firm*—Sterne, Kessler, Goldstein & Fox

[57] ABSTRACT

The present invention relates to a method of subgrouping media formulations into stable, compatible components that can then be solubilized at high concentrations (10× to 100×). Concentrated solutions of the ingredient containing subgroups can be used to prepare media formulations. Concentrated culture media formulations (2–10×) or 1× cell culture media can be prepared according to the present invention by mixing a sufficient amount of the concentrated subgroup solutions with a sufficient amount of a diluent (water, buffer, etc.). The present invention further relates to stabilization of glutamine by complexing or mixing glutamine with divalent metal cations in solution.

29 Claims, 4 Drawing Sheets

1 X 100 L DRUM

+

=     10,000 L

1 X 200 L DRUM

+

1 X 200 L DRUM

MEDIA CONCENTRATE TECHNOLOGY

This application is a continuation, of application Ser. No. 07/716,264, filed Jun. 17. 1991 now abandoned.

FIELD OF THE INVENTION

The present invention relates to the field of cell culture media and specifically to media ingredients subgrouped selectively into concentrated, compatible formulations. Such concentrated formulations are stable and can be used to prepare cell culture media.

BACKGROUND OF THE INVENTION

Cell culture medium provides the nutrients necessary to maintain and grow cells in a controlled, artificial and in vitro environment. Characteristics and compositions of the cell culture media vary depending on the particular cellular requirements. Important parameters include osmolarity, pH, and nutrient formulations.

Media formulations have been used to grow a number of cell types including animal, plant and bacterial cells. Cells grown in culture media catabolize available nutrients and produce useful biological substances such as monoclonal antibodies, hormones, growth factors and the like. Such products have therapeutic applications and, with the advent of recombinant DNA technology, cells can be engineered to produce large quantities of these products. Thus, the ability to grow cells in vitro is not only important for the study of cell physiology, it is necessary for the production of useful substances which may not otherwise be obtained by cost-effective means.

Cell culture media formulations have been well documented in the literature and a number of media are commercially available. Typical nutrients in cell culture media include amino acids, salts, vitamins, trace metals, sugars, lipids and nucleic acids. Often, particularly in complex media compositions, stability problems result in toxic products and/or lower effective concentrations of required nutrients, thereby limiting the functional life-span of the culture media. For instance, glutamine is a constituent of almost all media that are used in culturing of mammalian cells in vitro. Glutamine decomposes spontaneously into pyrrolidone carboxylic acid and ammonia. The rate of degradation can be influenced by pH and ionic conditions but in cell culture media, formation of these breakdown products cannot be avoided (Tritsch et al., *Exp. Cell Research* 28:360–364 (1962)).

Wang et al. (*In Vitro* 14:(8):715–722 (1978)) have shown that photoproducts such as hydrogen peroxide, which are lethal to cells, are produced in Dulbecco's Modified Eagle's Medium (DMEM). Riboflavin and tryptophan or tyrosine are components necessary for formation of hydrogen peroxide during light exposure. Since most mammalian culture media contain riboflavin, tyrosine and tryptophan, toxic photoproducts are likely produced in most cell culture media.

To avoid these problems, researchers make media on an "as needed" basis, and avoid long term storage of the culture media. Commercially available media, typically in dry powder form, serves as a convenient alternative to making the media from scratch, i.e., adding each nutrient individually, and also avoids some of the stability problems associated with liquid media. However, only a limited number of commercial culture media are available, except for those custom formulations supplied by the manufacturer.

Although dry powder media formulations may increase the shelf-life of some media, there are a number of problems associated with dry powdered media, especially in large scale application. Production of large media volumes requires storage facilities for the dry powder media, not to mention the specialized media kitchens necessary to mix and weigh the nutrient components. Due to the corrosive nature of dry powder media, mixing tanks must be periodically replaced.

There exists a need to lower the cost of production of biological substances. Efficient and cost effective methods to stabilize liquid cell culture media as well as the development of convenient methods to produce 1× media formulations would be an important development in the field of cell culture media technology.

SUMMARY OF THE INVENTION

The present invention relates to a method of subgrouping media formulations into stable, compatible components that can then be solubilized at high concentrations (10× to 100×) in solution containing, for example, water, acid, alkali or alcohol, depending on the subgroup. Any media formulation can be divided into one or more of the six subgroups of the present invention. Specific subgroups include an acid soluble subgroup, a glutamine containing subgroup, an alkali soluble subgroup, an alcohol soluble subgroup, a weak acid-base soluble subgroup and a supplement-containing subgroup.

According to the present invention, one of ordinary skill in the art may divide ingredients of a cell culture media into one of the subgroups of the present invention based on the physical and chemical properties (physicochemical properties) of each ingredient. Ingredients of culture media typically include amino acids, salts, vitamins, trace metals, sugars, lipids, nucleic acids and the like. These ingredients have different solubility and stability characteristics. Based on these characteristics, a classification scheme has been developed to permit the compatible subgrouping of media ingredients.

The invention thus relates to a method of subgrouping compatible media ingredients. Media ingredients, subgrouped in this manner, are stable and remain soluble even at high concentrations. Such concentrated solutions of the ingredient containing subgroups can then be used to prepare diluted media formulations suitable for growing or maintaining cells. Concentrated culture media formulations (2–10×) or 1× cell culture media can be prepared according to the present invention by admixing sufficient amount of the concentrated subgroup solutions with a sufficient amount of a diluent (water, buffer, etc.). Thus, the present invention is directed to a method of preparing a cell culture media comprising:

(a) dividing the compatible ingredients of a cell culture media into one or more subgroups, such subgroups comprising:
  (i) an acid soluble subgroup,
  (ii) a weak acid-base soluble subgroup,
  (iii) a glutamine-containing subgroup,
  (iv) an alcohol soluble subgroup,
  (v) an alkali-soluble subgroup, and
  (vi) a supplement-containing subgroup;

(b) dissolving each of the subgroups of compatible ingredients in a carrier to give concentrated solutions of the subgroup in the respective carrier; and (c) admixing a sufficient amount of each of the subgroups obtained in step (b) with a sufficient amount of a diluent to produce the cell culture media.

Furthermore, the present invention is specifically directed to a method of preparing RPMI-1640 media comprising:
  (a) dividing the ingredients of RPMI-1640 media into
    (i) an acid soluble subgroup,
    (ii) a weak acid-base soluble subgroup, and
    (iii) a glutamine-containing subgroup;
  (b) dissolving each of the subgroups of compatible ingredients in a carrier to give concentrated solutions of the subgroup in the respective carrier; and
  (c) admixing a sufficient amount of each of the subgroups obtained in step (b) with a sufficient amount of a diluent to produce the RPMI-1640 media.

This method can also be used to make DMEM media. That is, the ingredients of DMEM media can be divided into an acid soluble subgroup, a weak acid-base soluble subgroup and a glutamine-containing subgroup which are combined at some later time and diluted to give a 1× formulation.

The present invention further relates to stabilization of glutamine by complexing or mixing glutamine with divalent metal cations in solution. Thus, the present invention is also directed to a composition of matter comprising glutamine and a divalent cation in an amount effective to stabilize the glutamine.

Unexpectedly, the present invention provides for the preparation of media at dramatically reduced cost. The cost reductions are due to the following factors: The media concentrates of the present invention may be produced with much smaller production facilities since the large stir tanks required for 1× medias are not required. In addition, the media concentrates of the present invention may be prepared on an as needed basis using "just in time" production techniques which reduce inventory, storage and labor costs. The time required for the preparation and shipping of the media may be reduced from 6–8 weeks to as little as one day. In addition, the media concentrates of the present invention may be prepared without the use of ball milling machines since each of the subgrouped ingredients is readily soluble. In addition, the media subgroups of the present invention may be stored at room temperature which eliminates the need for refrigeration. In addition, the present invention allows for the preparation of concentrates which may be used to prepare very large quantities of 1× media (100,000 liters or greater) which require only one quality control test compared to multiple quality control tests for multiple batches produced according to the prior art. Importantly, the media concentrates of the present invention are much more consistent between batches since the subgrouped components are more stable. Thus, the present invention is a great advance in the art of media formulation.

DESCRIPTION OF THE PREFERRED EMBODIMENTS

Figure 1:
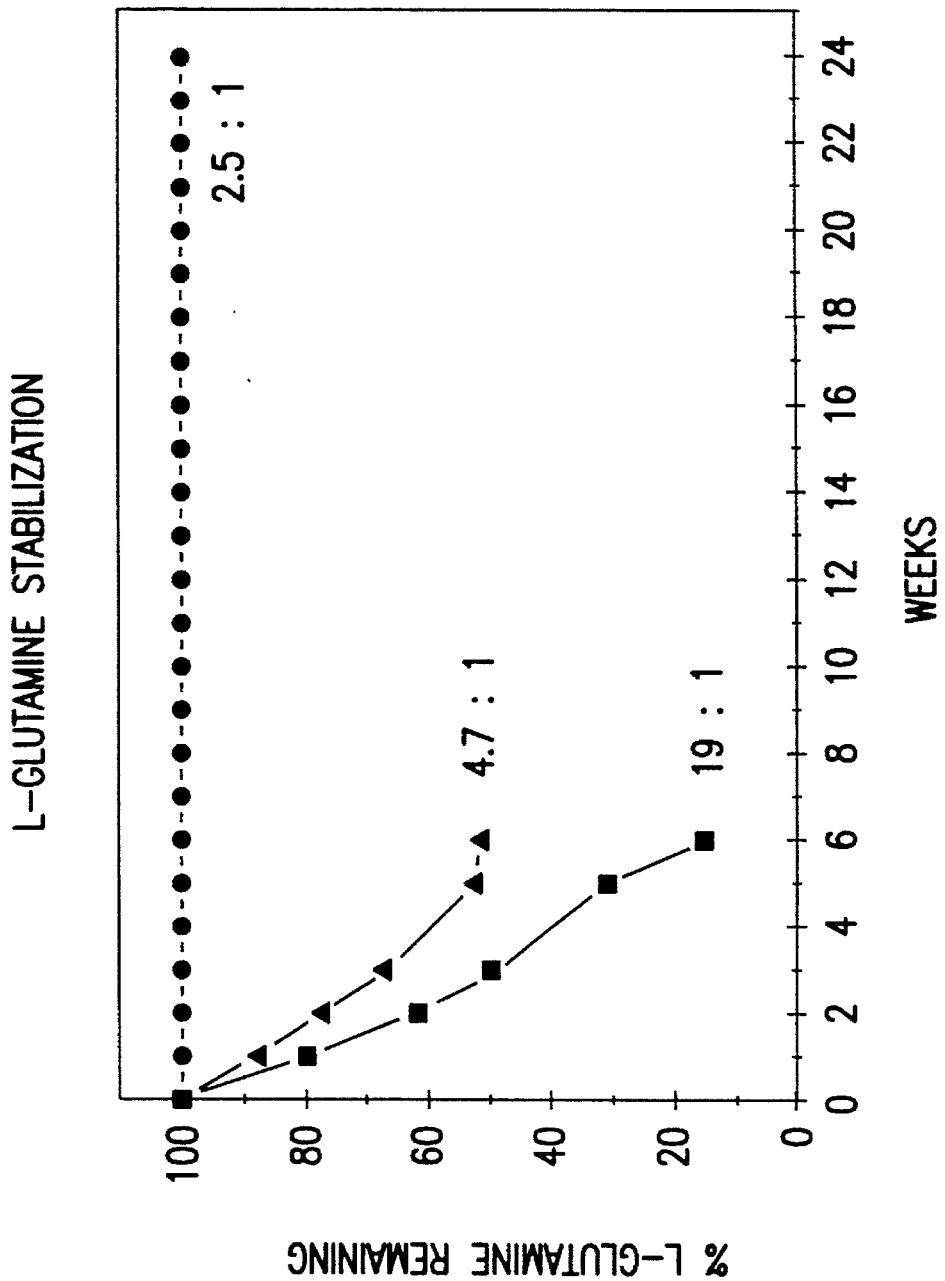
FIG. 1 shows L-glutamine stabilization in solution. Various ratios of L-glutamine to divalent cations were tested and the stability of L-glutamine was determined.

In the description that follows, a number of terms conventionally used in the field of cell culture media are utilized extensively. In order to provide a clear and consistent understanding of the specification and claims, and the scope to be given such terms, the following definitions are provided.

Ingredients.

The term "ingredients" refer to any compound, whether of chemical or biological origin, that can be used in cell culture media to maintain or promote the growth or proliferation of cells. The terms "component", "nutrient" and "ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain growth of cells in vitro can be selected by those of skill in the art, in accordance with the particular need.

Cell Culture.

By "cell culture" is meant cells or tissues that are maintained, cultured or grown in an artificial, in vitro environment.

Culture vessel.

Glass, plastic or metal containers of various sizes that can provide an aseptic environment for growing cells are termed "culture vessels."

Cell Culture Media.

The phrases "cell culture media" or "culture media" or "media formulation" refer to a nutritive solution for culturing or growing cells. The ingredients that compose such media may vary depending on the type of cell to be cultured. In addition to nutrient composition, osmolarity and pH are considered important parameters of culture media.

Compatible Ingredients.

Each ingredient used in cell culture media has unique physical and chemical characteristics. By "compatible ingredients" is meant those media nutrients which can be maintained in solution and form a "stable" combination. A solution containing "compatible ingredients" is said to be "stable" when the ingredients do not degrade or decompose substantially into toxic compounds, or do not degrade or decompose substantially into compounds that can not be utilized or catabolized by the cell culture. Ingredients are also considered "stable" if degradation can not be detected or when degradation occurs at a slower rate when compared to decomposition of the same ingredient in a 1× cell culture media formulation. Glutamine, for example, in 1× media formulations, is known to degrade into pyrrolidone carboxylic acid and ammonia. Glutamine in combination with divalent cations are considered "compatible ingredients" since little or no decomposition can be detected over time.

Compatibility of media ingredients, in addition to stability measurements, are also determined by the "solubility" of the ingredients in solution. The term "solubility" or "soluble" refers to the ability of an ingredient to form a solution with other ingredients. Ingredients are thus compatible if they can be maintained in solution without forming a measurable or detectable precipitate. Thus, the term "compatible ingredients" as used herein refers to the combination of particular culture media ingredients which, when mixed in solution either as concentrated or 1× formulations, are "stable" and "soluble."

1× Formulation.

A cell culture media is composed of a number of ingredients and these ingredients vary from media to media. A "1× formulation" is meant to refer to any aqueous solution that contains some or all ingredients found in a cell culture media. The "1× formulation" can refer to, for example, the cell culture media or to any subgroup of ingredients for that media. The concentration of an ingredient in a 1× solution is about the same as the concentration of that ingredient found in the cell culture formulation used for maintaining or growing cells. Cell culture media used to grow cells is a 1× formulation by definition. When a number of ingredients are present (as in a subgroup of compatible ingredients), each ingredient in a 1× formulation has a concentration about equal to the concentration of those ingredients in a cell culture media. For example, RPMI 1640 culture media contains, among other ingredients, 0.2 g/l L-arginine, 0.05 g/l L-asparagine, and 0.02 g/l L-aspartic acid. A "1× formulation" of these amino acids, which are compatible ingredients according to the present invention, contains about the same concentrations of these ingredients in solution. Thus, when referring to a "1× formulation," it is intended that each ingredient in solution has the same or about the same concentration as that found in the cell culture media being described. The concentrations of media ingredients in a 1× formulation are well known to those of ordinary skill in the art, See *Methods For Preparation of Media, Supplements and Substrate For Serum-Free Animal Cell Culture* Alan R. Liss, New York (1984), which is incorporated by reference herein in its entirety. The osmolarity and/or pH, however, may differ in a 1× formulation compared to the culture media, particularly when fewer ingredients are contained by the 1× formulation.

10× Formulation.

A "10× formulation" refers to a solution wherein each ingredient in that solution is about 10 times more concentrated than the same ingredient in the cell culture media. RPMI 1640 media, for example, contains, among other things, 0.3 g/l L-glutamine. By definition, a "10× formulation" contains about 3.0 g/l glutamine. A "10× formulation" may contain a number of additional ingredients at a concentration about 10 times that found in the 1× culture media. As will be apparent, "25× formulation," "50× formulation" and "100× formulation" designate solutions that contain ingredients at about 25, 50 or 100 fold concentrations, respectively, as compared to a 1× cell culture media. Again, the osmolarity and pH of the media formulation and concentrated formulation may vary.

A. Media Concentrate Technology

The Media Concentrate Technology of the present invention is based on the subgrouping of media ingredients into stable, compatible components that can then be solubilized into concentrated formulations (10×–100×) by the dissolution in an appropriate quantity of a carrier such as water, aqueous acid, alcohol or aqueous alkali, depending on the particular subgroup. Such solutions are referred to herein as a "carrier". Under appropriate conditions, these subgroups can be reconstituted (admixed) to produce a concentrated (greater than 1×) cell culture media formulation, such as a 2× to 10×, or reconstituted directly to a 1× cell culture media formulation. The concentrate media technology of the present invention is related to the subgrouping of compatible components, production of liquid concentrates of such subgroups, and mixing sufficient amounts of these concentrated subgroups with a sufficient amount of a diluent to produce a desired media formulation.

Cell culture media formulations are made up of amino acids, salts, vitamins, trace metals, sugars, lipids, nucleic acids, etc. Each of these components has different solubility and stability properties. Amino acids, for example, (except for glutamine) are soluble and very stable under acidic conditions (pH of about 1.0) while vitamins (except for thiamine and ascorbic acid) are solubilized under dilute acid or alkaline conditions (pH of about >4.0). Based on the physical properties of media ingredients, a classification scheme was developed that permits the subgrouping of any media formulation which can be used to prepare stable liquid concentrates.

The present invention defines six subgroups in which compatible ingredients from any cell culture media can be divided. The ingredients of a given cell culture media formulation can be separated into at least one of the subgroups defined by the present invention. Each subgroup, containing the compatible media ingredients, can then be dissolved in a liquid carrier or maintained in dry form. The type of liquid carrier and the method used to dissolve the grouped ingredients into solution vary depending on the subgroup and can be determined by one of ordinary skill in the art with no more than routine experimentation.

Preferably, the solutions comprising the subgrouped ingredients are more concentrated than the concentration of the same ingredients in a 1× media formulation. The grouped ingredients are preferably 25 fold more concentrated (25× formulation) and most preferably 50 fold more concentrated (50× formulation). Higher concentrated formulations can be made provided that the ingredients remain soluble and stable.

Once the media ingredients have been divided into the one or more of the six subgroups and prepared as separate concentrated solutions, an appropriate (sufficient) amount of each concentrate is combined with a diluent to produce a 1× media formulation. Typically, the diluent used is water but other solutions including aqueous buffers, aqueous saline solution, or other aqueous solutions containing particular media ingredients may be used according to the invention.

The culture media of the present invention is typically sterilized to prevent unwanted contamination of the cell culture media. Sterilization may be accomplished, for example, by pasteurization after admixing the concentrated ingredients to produce a sterile culture media. Alternatively, each concentrated subgroup may be sterilized and stored as a sterile solution. These sterile concentrates can then be mixed with a sterile diluent to produce a concentrated 1× sterile media formulation.

One of a number of commonly used sterilization techniques may be used to sterilize the concentrated subgroups or the media formulations of the present invention. Sterilization techniques will vary depending on the properties of the solutions to be sterilized. Typical sterilization techniques, according to the present invention, include heat and/or filter sterilization. Other types of sterilization will be readily apparent to one of ordinary skill in the art.

B. Type of Media

Any type of cell culture media can be made according to the present invention. Culture media formulations are well-known in the literature and a number are commercially available. New media formulations and known media formulations which have been modified can also be prepared according to the present invention. That is, the media ingredients can be divided into compatible subgroups as defined in the present invention. The subgroups of these ingredients can then be concentrated in solution and, if desired, sterilized.

Examples of cell culture media that can be prepared according to the present invention include, but are not limited to, DMEM, RPMI-1640, DMEM/F12, IMDM, MEM, M199, McCoy's 5A, and F12 Nutrient Mixture (GIBCO/BRL CATALOGUE & PREFERENCE GUIDE (1990)).

The present invention thus provides a means for making one or more concentrated solutions of compatible ingredients, which when sufficient amounts are mixed in combination with sufficient amounts of diluent, a cell culture media may be produced.

Any ingredient employed in a cell culture media can be divided into one or more of the six subgroups of the present invention. Although the list of ingredients described herein and contained by each subgroup may not be all-inclusive, one of skill in the art can easily determine, by knowing the physicochemical properties of the ingredient, which subgroup contains other ingredients compatible with that ingredient. Alternatively, if the properties of the new ingredient are not known, routine experimentation can be used to determine the preferred subgroup. For example, each subgroup containing particular media ingredients as defined according to the present invention, can be supplemented with the new ingredient. The new ingredient will be compatible with a particular subgroup when the resultant concentrated solution is soluble and stable. By comparing experimental media preparations to control media not made according to the media concentrate technology, one of skill may further determine the preferred subgroup. Growth characteristics of cells, formation of toxic products, and shelf-life of the media may be used as indicators of compatible ingredients.

Particular ingredients that have unique physicochemical properties may, in some situations, not be compatible with the ingredients of any subgroup. In such a case, it may be necessary to maintain this component as a separate subgroup. Such ingredients may be added to the diluent in an appropriate concentration so that a desired 1× culture media (containing this ingredient) is produced when sufficient amounts of the concentrated subgroups are admixed with the diluent. Alternatively, the incompatible ingredient can be added as a separate concentrated solution. Thus, the present invention envisions the development of additional subgroups, other than those defined in the present invention, which stabilize and solubilize additional ingredients which may not be compatible with any subgroups defined herein.

It will be apparent from the list of ingredients designated for each subgroup described below that a number of ingredients can be included in more than one subgroup. When a particular ingredient is designated as compatible with two or more subgroups, that ingredient can be included in one or more of these subgroups at various concentrations, as long as the total amount of that ingredient conforms to the final media formulation. The only limitation is that the amount of ingredient added does not adversely affect solubility or stability of the other ingredients in the particular subgroup. The number and types of subgroups necessary to prepare different media may vary according to media complexity and/or the physicochemical properties of the ingredients. The duplication of ingredients in more than one subgroup thus provides one of ordinary skill in the art with a versatile classification scheme to prepare any media.

C. Acid Soluble Subgroup

Media ingredients placed in the acid soluble subgroup comprise all amino acids (except glutamine), thiamine, ascorbic acid, ferric compounds, ferrous compounds, purines, glutathione and monobasic sodium phosphates. These components are soluble in acid (pH of about 0 to 1.0) and are very stable under these conditions.

Both D and/or L-amino acids may be included in the acid-soluble subgroup of the present invention. Typically, culture medium contain the L-amino acids. As required by the desired media formulation, one or more amino acids in any combination may be included in the acid-soluble subgroup, with the exception of glutamine. Glutamine is specifically included in the glutamine-containing subgroup. Thus, the amino acids that may be included in the acid-soluble subgroup of the present invention, depending on the requirements of the desired culture media, include glycine, alanine, valine, leucine, isoleucine, serine, threonine, cysteine, cystine, methionine, asparagine, aspartic acid, glutamic acid, lysine, arginine, phenylalanine, tyrosine, proline, hydroxyproline, histidine, and tryptophan. Derivatives of amino acids may also be included in the acid-soluble group provided that the derivative is compatible with the other ingredients of this subgroup and with the maintenance or proliferation of the particular cell culture.

Other ingredients which may be included in the acid-soluble subgroup of the present invention include thiamine (vitamin $B_1$), ascorbic acid (vitamin C), purines (guanine and adenine) and glutathione. Derivatives of such compounds are well-known and may be included in the acid-soluble group, provided that the physicochemical properties have not been changed to the extent that the derivative is no longer compatible with the other ingredients included in this subgroup and with the maintenance or proliferation of the particular cell culture.

Ferric and ferrous compounds, if required by the media formulation, may be placed into this subgroup as well. Such ferric and ferrous compounds, that are stable and soluble in the presence of the other ingredients included in this subgroup, can easily be determined by one of skill in the art. Examples of such ferrous or ferric compounds include, but are not limited to, $Fe(NO_3)_3$, $FeSO_4$, and $FeCl_3$.

Any monobasic phosphate which is a component of the desired media formulation can be contained within the acid-soluble subgroup. Examples of typical phosphates include, but are not limited to, monobasic phosphates such as $NaH_2PO_4$ and $KH_2PO_4$.

The acid-soluble subgroup of the present invention may contain various combinations of the above-noted compatible ingredients, as required by the particular culture media. Thus, according to the classification scheme of the present invention, the ingredients found in the desired culture media are selected which are compatible in an acid solution. Once divided in this manner, these ingredients, typically in dry powder form (dehydrated), are dissolved in an acidic solution with a pH of about 0 to 1.0. Preferably, the resulting solution is concentrated (10× to 100×). That is, the ingredients in the acid solution are more concentrated then the same ingredients found in a 1× media formulation.

As will be apparent, the concentrated acid-soluble subgroup may vary slightly in composition, osmolarity and pH from preparation to preparation of the same media. Furthermore, the acid-soluble subgroup will also differ from one media to the next. This is true for the other subgroups as well. The present invention provides the means to produce a stable preparation containing acid-soluble media ingredients. Such a preparation can be maintained as a dry powder mix of ingredients but preferably are maintained as a concentrated solution. Typically, the concentrated solution comprising the acid soluble subgroup is sterilized by one of a number of wellknown techniques.

D. Glutamine Containing Subgroup

Glutamine is considered an unstable component in liquid media (Tritsch, G. L. et al., *Experimental Cell Research* 28:360–364 (1962); Ozturk, S. S. et al., *Biotechnol. Prog.* 6:121–128 (1990)). In solution, glutamine decomposes to pyrrolidone carboxylic acid and ammonia. The advent of media concentrate technology according to the present invention provides a procedure for the stabilization of glutamine. Thus, cell culture media that contains glutamine can be made by preparing, in addition to other subgroups, a glutamine-containing subgroup.

According to the invention, glutamine (both D and L-forms) can be stabilized in solution by the addition of one or more divalent cations. Any divalent cation, such as $Ca^{+2}$, $Mg^{+2}$, $Mn^{+2}$, $Zn^{+2}$, and $Cu^{+2}$ can be used to stabilize glutamine. A number of readily available salts including, but not limited to, $MgCl_2$, $CaCl_2$, $Ca(NO_3)_2$, and $MgSO_4$ may supply these divalent cations. Thus, any compatible calcium salt, magnesium salt, and/or manganese salt may be included in this subgroup. Such salts are typical ingredients of almost any media. Therefore, the divalent salts of the media formulation should be included in this subgroup to stabilize glutamine. In situations where divalent cations are generally not ingredients of the desired culture media, divalent cations that do not adversely affect the growth or the maintenance of the cells to be grown should be added to stabilize glutamine in the glutamine-containing subgroups.

The only limitation, however, with regard to the glutamine-containing subgroup of the invention is that potassium salts such as potassium chloride cannot be included in this group. Sodium and magnesium ions decrease the solubility of potassium ions. Additionally, metal salts of phosphate cannot be put into this group since $Ca^{2+}$ forms an insoluble complex with phosphate, removing $Ca^{2+}$ from the solution.

The amount of glutamine as required by the particular media is mixed with a sufficient amount of a divalent cation to stabilize glutamine. The ratio of glutamine to divalent cations in this subgroup is preferably about 2:1 (weight to weight) but may range from 2:1 to 2.9:1. The pH of such a solution is also important for stabilizing glutamine. The preferred pH may range from 4.0 to 6.0. The most preferred pH of the glutamine-divalent cation solution is about 5.5. Basic pHs tend to lower glutamine stability, and thus, if necessary, pH may be adjusted with an acid which is compatible with the glutamine containing subgroup, e.g. HCl.

When the ratio of glutamine to divalent cation is about 2:1, glutamine forms a stable soluble complex. This complex does not favor the breakdown of glutamine to pyrrolidone carboxylic acid and ammonia. The glutamine metal complex thus provides a means for supplying this essential nutrient in a stable, soluble liquid form.

The ingredients contained in the glutamine-containing subgroup may comprise glutamine, calcium salts, and/or magnesium salts. D-Ca pantothenate may also be included in the glutamine containing subgroup, as well as sodium chloride.

As will be evident, each culture medium prepared according to the present invention may have a preferred osmolarity range. Osmolarity will change, as will the final pH of the culture media, with the amount of acid/base used for solubilization of ingredients in each subgroup. One of skill in the art can easily determine the amount of salt, e.g., sodium chloride, necessary to obtain the preferred final osmolarity of the desired culture media by taking into consideration the final pH and volume of each concentrated subgroup required to prepare the media formulation. Such parameters (pH of each subgroup and total salt content) can be easily determined by routine experimentation. For example, the pH of the ingredient containing subgroups can be measured by well-known techniques. The osmolarity of the 1× media formulation, prepared by mixing an appropriate volume of these concentrated subgroups allows one of ordinary skill in the art to determine the amount of sodium chloride needed, if any, to adjust the final osmolarity of the culture media. This amount of sodium chloride may be added to the glutamine-containing subgroup to achieve the proper final osmolarity. Most 1× media formulations have broad range requirements for final osmolarity and pH and therefore slight variations in subgroup pH and salt concentration are not critical.

E. Weak Acid and Base Soluble Subgroup

The media ingredients of the weak acid-weak base soluble subgroup (referred to herein as a weak acid-base soluble subgroup) consist of sugars, deoxyribose, ribose, nucleosides, water-soluble vitamins (except for thiamine, ascorbic acid and Ca-pantothenate) riboflavin, salts, e.g., potassium chloride and sodium chloride, trace metals, lipids, acetate salts, phosphate salts, HEPES, phenol red, pyruvate salts, and buffers.

The pH of the weak acid-base subgroup may range from about 4.0–9.0. Dibasic sodium phosphate and some monobasic sodium phosphate may also be grouped here. The combination of dibasic and monobasic sodium phosphate provides a buffer system for this concentrated subgroup. Adjustment of pH to the solution of this subgroup is preferably made by the addition of sodium hydroxide or hydrochloric acid, as appropriate, but not potassium hydroxide.

The ingredients found in this subgroup are determined, as with all other subgroups, by the media composition. Thus, any combination of the above ingredients may be included in the weak acid-base soluble group.

Sugars that are included in this subgroup include any sugar that can be used as a media ingredient and is compatible in combination with one or more of the above ingredients. Such sugar compounds include glucose, galactose, maltose, mannose, etc., and derivatives thereof.

Sugars in this subgroup may also serve as a vehicle for solubilizing lipids, if lipids are included in this subgroup. Lipids can be solubilized in solution after being desiccated onto a sugar or salt molecule. Briefly, lipids are solubilized in a small volume of ethanol and then slowly dripped onto a dry powder of sugar/salt. The mixture is dried for 3 hours and then ball milled. The sugar-lipid or salt-lipid composition can then be prepared as a concentrate comprising the other ingredients of the weak acid-base subgroup.

Any lipid and/or fat soluble ingredient including, but not limited to, linoleic acid, lipoic acid, cholesterol, calciferol, vitamin A, 2-mercaptoethanol, Tween 80, menadione and vitamin E can be desiccated onto a salt or sugar and thus included in this subgroup.

Any deoxyribose, ribose or nucleoside may be included in the weak acid and base soluble subgroup according to the present invention. These compounds and their derivatives are well-known. Examples include adenosine and adenosine triphosphate. Again, the only limitation is that the ingredient must be compatible with the other ingredients found in this subgroup.

Vitamins in the weak acid-base subgroup may include all water-soluble vitamins and their derivatives except thiamine, ascorbic acid and Ca-pantothenate. Such water-soluble vitamins that may be included in the weak acid-base soluble group include folic acid, biotin, pyridoxine, nicotinic acid, riboflavin, and the like.

Trace metals, used in media formulations, are also included in this subgroup. Examples of trace metals include $CuSO_4$, $Na_2SeO_3$, $ZnSO_4$, and $CoCl_2$. Trace amounts of other metals may also be included in this group. The selection of appropriate trace metals and the amounts employed may be readily determined by one of ordinary skill in the art.

Potassium chloride, dibasic sodium phosphate, sodium acetate, phenol red, sodium chloride, HEPES, and sodium pyruvate are also compatible ingredients in the weak acid-base subgroup. Derivatives of any of the compounds can also be employed in this group as long as such derivatives are compatible.

Riboflavin may also be placed in this group. Riboflavin is a photosensitizer and is the main nutrient responsible for the generation of hydrogen peroxides through the interaction with histidine, methionine, tyrosine and tryptophan (Griffin, F. M., et al., *Cancer Research* 91:2241–2248 (1981); Wang, R. J., et al., *In Vitro* 14:715–722 (1978)). By separating riboflavin from the amino acids, a stable concentrated subgroup is created.

A component that lends stability to liquid media subgroup comprising riboflavin is pyruvate. Pyruvate interacts with hydrogen peroxide to give acetic acid, carbon dioxide and water (Weil, L., Gordon, W. G., and Buchert, A. R., *Arch. Biochem. Biophys.* 33:90–109 (1951)). Since hydrogen peroxide is deleterious to cultured cells, membrane proteins, lipids and enzymes, controlling its build-up may be critical in a particular media. Thus, even if the desired media does not require pyruvate, the addition of pyruvate helps to increase the stability of the weak acid-base soluble subgroup and the shelf-life of the media prepared from this subgroup.

F. Alcohol Soluble Subgroup

Media formulations that contain cholesterol, steroids, Tween 80, fat-soluble vitamins or other hydrophobic components may be concentrated into an alcohol-soluble group. Other hydrophobic compounds may be included in the alcohol-soluble group are well known to those of skill in the art.

Any combination of these components can be solubilized in a small volume of ethanol or propylene glycol. Once solubilized, these ingredients are then microfluidized by well known techniques to form small lipid vesicles (Lidgate et al., *Bio Pharm.* 2(9): 28–33 (1989)). Briefly, the microfluidizer (Model 110 Microfluidizer) produces emulsions by combining shear, turbulence, and cavitation forces. Each cycle through the microfluidizer decreases the emulsion's mean droplet size ultimately producing submicron particles that are very stable. Water soluble components can also be trapped into these vesicles and then delivered to the culture media.

Fat soluble vitamins including vitamin A, D, E and K may also be included in this subgroup, as well as their derivatives. Steroids and their derivatives including cortisol, progesterone, estrogen, testosterone etc. are also included within the alcohol-soluble subgroup.

Fatty acids and lipids of the media formulation may be divided into this subgroup. Any fatty acid such as linoleic acid, oleic acid, arachidonic acid etc. fall into this classification. As will be appreciated, any lipid may also be included. Examples of lipids are locithin, sphingomyelin and phospholipids. Lipids (oils) are usually necessary ingredients in this subgroup since microfluidization requires lipids (oils) to prepare lipid vesicles. In situations where the media formulation requires lipids but not the hydrophobic ingredients of this subgroup, it may be unnecessary to prepare an alcohol-soluble subgroup since such lipids can be included in the weak acid-base soluble group. In the weak acid-base soluble subgroup, lipids are desiccated onto sugars and/or salts.

Other media components that may be included in the alcohol-soluble group of the present invention may include Tween 80 and 2-mercaptoethanol.

G. Alkali-Soluble Subgroups

For media components that require an alkaline environment for solubilization (pH 9.0), an alkali soluble subgroup is employed. This subgroup consists of the pyrimidines and purines that are stable and soluble at alkaline pH. These components, when dissolved in NaOH, form sodium salts which are soluble in an aqueous environment.

Pyrimidines and their derivatives that are compatible in this alkali subgroup include uracil and thymine. Xanthine and hypoxanthine are examples of purines that may also be include the alkali soluble subgroup of the present invention. Other ingredients that are stable and soluble in this alkali environment are known by or easily determined by those of skill in the art.

H. Supplement-Containing Subgroup

As previously stated, typical medium formulations comprise amino acids, salts, vitamins, trace metals, sugars, lipids and nucleic acids. However, media are often supplemented with proteins, antibiotics or undefined broths/sera. When such a supplement is required for a particular medium, the supplement can be used directly (e.g., serum) or made into a concentrate (protein solutions such as insulin, transferrin and growth factors). The supplement-containing subgroup can then be combined with the other concentrated subgroups to produce the desired media formulation.

A number of components that are included in the final media formulation, but not classified as a compatible ingredient in one of the aforementioned subgroups, may be added as one or more separate supplements. Thus, the present invention envisions the preparation of one or more supplement-containing subgroups that are not compatible in the above-noted subgroups. Such components that fall into the supplement subgroup include serum (fetal, horse, calf, etc.), yeastolate ultrafiltrate, tryptose phosphate broth, protein concentrates (insulin, transferrin, growth factors, hormones, albumin, etc.), antibiotics (gentamicin, penicillin, streptomycin, amphotericin B, etc.), whole egg ultrafiltrate, attachment factors (fibronectin, vitronectin, collagen, laminin, etc.) and $NaHCO_3$ liquid concentrate (for example, 25×). Depending on the final media formulation, one of ordinary skill in the art may select appropriate supplements which are compatible.

I. Kits

The subgroups of compatible ingredients of the invention are ideally suited for preparation of a kit. Such a kit may comprise a carrier means being compartmentalized to receive in close confinement one or more container means such as vials, test tubes, bottles, drums, and the like. Each of said container means comprises one of the individual subgroups of compatible ingredients as defined above. Such subgroups may be hydrated or dehydrated but are typically a concentrated liquid solution. Such solutions may, according to the invention, be sterile.

A first container means may, for example, comprise any combination of media ingredients that are compatible in the acid-soluble subgroup. Compatible ingredients or any combination thereof that are included in the weak acid-base soluble group may be contained in a second container means. A third and fourth container means may comprise any combination of ingredients included in the alkali-soluble subgroup and alcohol-soluble subgroup, respectively. A fifth container means may comprise any combination of ingredients included in the glutamine-containing subgroup as long as divalent cations are included to stabilize the glutamine. A sixth container means may comprise ingredients listed in the supplement-containing subgroup. Other ingredients that are not compatible in the defined subgroups of the invention may be contained in one or more further container means to avoid mixing of incompatible components.

The number and types of subgroup containing container means comprising a kit for making a cell culture media may vary depending on the type of media to be prepared. Typically, the kit will contain the respective container means containing the subgroups necessary to make a particular media. However, additional subgroup containing container means may be included in the kit of the invention so that different media can be prepared by mixing different amounts of various subgroups to make different media formulations.

J. Mixing Concentrated Subgroups to Prepare a Culture Media

The media concentrate technology of the present invention provides a means to prepare one or more concentrated solutions of compatible ingredients by dividing these ingredients into the subgroups defined above. These subgroups, once prepared as concentrated solutions (greater than 1×), can be combined with a diluent to prepare the desired culture media. The amount of concentrated solution and amount of diluent needed may vary depending on the concentration of each subgroup, the number of subgroups and the desired concentration of the final media. One of ordinary skill in the art can easily determine a sufficient volume of a diluent and a sufficient volume of these concentrated solutions to prepare the desired media.

The pH of the resulting culture media can be adjusted by addition of acid or base. The media, however, may not require any adjustment, especially if the pH of each subgroup concentrate is adjusted so that the pH of the prepared media is in the desired range. Osmolarity of the media can also be adjusted after mixing the concentrated solutions with a diluent. Typically, the desired osmolarity may be predetermined and adjustments in the salt concentration of the concentrated solutions may be made to prepare a final media with the desired osmolarity.

K. Uses

The present invention provides concentrates that can easily be mixed in sufficient amounts with a diluent to prepare a culture media. Mixing these concentrated subgroups can be done on a batch or continuous basis. In a batch system, appropriate amounts of the subgroup concentrates can be admixed with a diluent to prepare a single quantity of media. In a continuous system, sufficient amounts of each subgroup concentrate are continuously admixed with sufficient amounts of a diluent in a mixing chamber, while the culture media is continually removed. The obvious advantage of the continuous system is that a single reactor (mixing chamber) can be used to prepare media for a number of culture vessels or fermentation tanks. In addition, the continuous preparation of media in this manner can be accomplished in a closed sterile system.

According to the present invention, appropriate media concentrates can be prepared for any media and in any quantity. Such concentrates can thus be prepared and supplied commercially or made and used for in-house research. Customers that obtain prepared concentrates may prepare media in a more cost-effective manner. For example, the life of mixing tanks will be increased since certain corrosive dry powders need not be used to prepare media. Also, fewer man-hours may be needed to prepare the desired culture media.

Having now fully described the present invention, the same will be more clearly understood by reference to certain specific examples which are included herewith for purposes of illustration only, and not intended to be limiting of the invention, unless specified.

EXAMPLE I

Stabilization of Glutamine with Divalent Cations

L-Glutamine was admixed in a solution with varying amounts of calcium nitrate and magnesium sulfate at a pH of 5.5. FIG. 1 shows that when the ratio of L-glutamine to divalent cations is significantly above 2.5:1, the stability of glutamine decreased. L-Glutamine was assayed by precolumn derivatization with O-phthaldialdehyde and then detected using high performance liquid chromatography (Rajendra, W. *J. Liquid Chromat.* 10(5):941–955 (1987)).

At a 2.5:1 glutamine to divalent cation ratio, glutamine remained stable in solution for 24 weeks. Cell culture media containing glutamine also contains divalent cations but due to the interaction of divalent cations with other amino acids present in the culture media, glutamine was not stabilized in 1× media formulation and begins to slowly degrade at 4° C. with only 65–70% remaining after three weeks. (Sigma Cell Culture Reagents Catalogue (1991) pg. 202.)

EXAMPLE II

Preparation of RPMI-1640 Media

RPMI-1640 media is a media commonly used to grow mammalian cells in culture. The pH of this media is about 7.0 and the osmolarity can range from 265 to 300.

RPMI-1640 contains amino acids, including L-glutamine, various salts, vitamins, sugars, etc. The ingredients found in this media are described in GIBCO/BRL Catalogue and Reference Guide, pg. 118, 1990.

The ingredients of RPMI-1640 media were divided into a number of compatible subgroups. Once the dry powder compatible ingredients were mixed, a concentrated solution of each subgroup was prepared. An appropriate volume of each of the prepared concentrated subgroups was then used to prepare a 1× RPMI-1640 media formulation.

Table 1 shows the ingredients of the RPMI-1640 media that were divided into the acid soluble subgroup. The concentrations correspond to a 1× formulation in 1 liter of solution. To make a 100× formulation of the acid soluble subgroup, the amount of each ingredient shown in Table 1 was added together to prepare a dry powder mix (DPM) of acid soluble ingredients. For example, 0.2 g of L-arginine, 0.05 g L-asparagine, 0.02 g L-aspartic acid, etc. were added to prepare a dry powder mix totaling 0.69 grams.

TABLE 1

Acid-Soluble Subgroup for RPMI-1640 Media

| Component | Molecular Weight | g/l | µM |
|---|---|---|---|
| L-Arginine | 174 | .200 | 1,149.43 |
| L-Asparagine | 132 | .050 | 378.78 |
| L-Aspartic Acid | 133 | .020 | 150.37 |
| L-Cystine.2HCl | 313 | .06515 | 208.15 |
| L-Glutamic Acid | 147 | .020 | 136.05 |

TABLE 1-continued

Acid-Soluble Subgroup for RPMI-1640 Media

| Component | Molecular Weight | g/l | μM |
|---|---|---|---|
| Glycine | 75 | .010 | 133.33 |
| L-Histidine | 155 | .015 | 96.77 |
| L-Hydroxyproline | 131 | .020 | 152.67 |
| L-Isoleucine | 131 | .050 | 381.67 |
| L-Leucine | 131 | .050 | 381.67 |
| L-Lysine.HCl | 183 | .040 | 218.58 |
| L-Methionine | 149 | .015 | 100.67 |
| L-Phenylalanine | 165 | .015 | 89.82 |
| L-Proline | 115 | .020 | 173.91 |
| L-Serine | 105 | .030 | 285.71 |
| L-Threonine | 119 | .020 | 168.07 |
| L-Tryptophan | 204 | .005 | 24.51 |
| L-Tyrosine | 181 | .02086 | 115.32 |
| L-Valine | 117 | .020 | 170.94 |
| Thiamine.HCl | 337 | .001 | 2.967 |

As shown in Table 2, the acid soluble compatible ingredients were mixed with 8.8 ml of water and then HCl was added to give a final pH of 0.85. This required about 1.2 ml of 5N HCl. The resulting solution was a 100× formulation of the acid soluble subgroup for RPMI-1640 media.

Based on the 1640 media formulation, two additional subgroups were prepared: a glutamine-containing subgroup and a weak acid-base soluble subgroup. Table 3 shows the ingredients added to make a dry powder mix of the glutamine-containing subgroup for RPMI-1640 media. The mixture of ingredients totaling 6.4 g was mixed with about 17.5 ml water to prepare a 20 ml 50× concentrate with a final pH of about 5.5.

Table 4 shows the amount of ingredients needed to make 3.25 g of dry powder mix (DPM) for the weak acid-base soluble group. About 19.5 ml water was added to the weak acid-base ingredients to prepare a 20 ml solution with a pH of about 8.3. All ingredients in this subgroup were water soluble and therefore did not require desiccation onto a salt or sugar.

Reconstitution of the above-described acid-soluble subgroup, glutamine-containing subgroup and weak acid-base soluble subgroup was accomplished as shown in Table 2 to prepare a 1× RPMI-1640 media formulation. $NaHCO_3$ was added as a separate supplement. The osmolarity of the media was 276 mOm before filter sterilization. Alternatively, a concentrated solution of $NaHCO_3$ can also be used rather than adding dry powder $NaHCO_3$ to the reconstituted media.

TABLE 2

Procedure for Preparation of RPMI-1640 Subgroups

1. Weak Acid-Base Soluble Subgroup (50× Concentrate)
   Quantity sufficient to make 1 liter
   19.5 ml water
   3.25 g DPM 20.0 ml Total Volume   Final pH = 8.28
   Special Instructions: Add DPM slowly to water to avoid solidification of components. Use moderate stirring until dissolved (about 15–20 minutes).

2. Acid Soluble Subgroup (100× Concentrate)
   Quantity sufficient to make 1 liter
   8.8 ml water
   0.69 g DPM TABLE 2-continued 1.20 ml 5N HCl 10.0 ml Total Volume   Final pH = 0.85
   Special Instructions: Add 5N HCl slowly to the stirred solution.

3. Glutamine-Containing Subgroup (50× Concentrate)
   Quantity sufficient to make 1 liter
   17.5 ml water
   6.4 g DPM 20.0 ml Total Volume   Final pH = 5.50
   Special Instructions: This is an endothermic process. The temperature of the solution will drop about 3° C. with the addition of components. Use moderate stirring for about 10–15 minutes or until all components are dissolved.

Procedure for Preparing a 1× RPMI-1640 Media Formulation:

1. Add subgroup concentrates to water in the following order:
   A. 950 ml water                                    pH 5.98
   B. 20 ml Glutamine-Containing Subgroup             pH 5.61
   C. 20 ml Weak Acid-Base Soluble Subgroup           pH 8.20
   D. 10 ml Acid Soluble Subgroup                     pH 4.91
   E. 2.0 g $NaHCO_3$                                 pH 7.00
      Osmolarity before filtration: 276 m OSm

TABLE 3

Glutamine-Containing Subgroup for RPMI-1640 Media

| Component | Molecular Weight | g/l | μM |
|---|---|---|---|
| $Ca(NO_3)_2$ | 164.10 | .0695 | 423.52 |
| $MgCl_2$ | 95.23 | .0386 | 405.75 |
| NaCl | 58.44 | 6.000 | 102,669.4 |
| L-Glutamine | 146.00 | .300 | 2,054.79 |
| D—Ca Pantothenate | 476.00 | .0025 | 0.525 |

TABLE 4

Weak Acid-Base Soluble Subgroup for RPMI-1640 Media

| Component | Molecular Weight | g/l | μm |
|---|---|---|---|
| Biotin | 244.00 | .0002 | .8196 |
| Choline Chloride | 140.00 | .0030 | 21.4300 |
| Folic Acid | 441.00 | .0010 | 2.2670 |
| i-inositol | 180.00 | .0350 | 194.4400 |
| Niacinamide | 122.00 | .0010 | 8.1960 |
| Para-Aminobenzoic Acid | 137.13 | .0010 | 7.2900 |
| Pyridoxine-HCl | 206.00 | .0010 | 4.8540 |
| Riboflavin | 376.00 | .0002 | .5320 |
| Vitamin B12 | 1355.00 | .000005 | .00369 |
| Glucose | 180.16 | 2.0000 | 11,101.2400 |
| Glutathione | 307.33 | .0010 | 3.2500 |
| Phenol Red | 376.36 | .0050 | 13.2900 |
| $Na_2HPO_4$ | 141.96 | .8000 | 5635.3900 |
| KCl | 74.56 | .4000 | 5364.8100 |

EXAMPLE III

Figure 2:
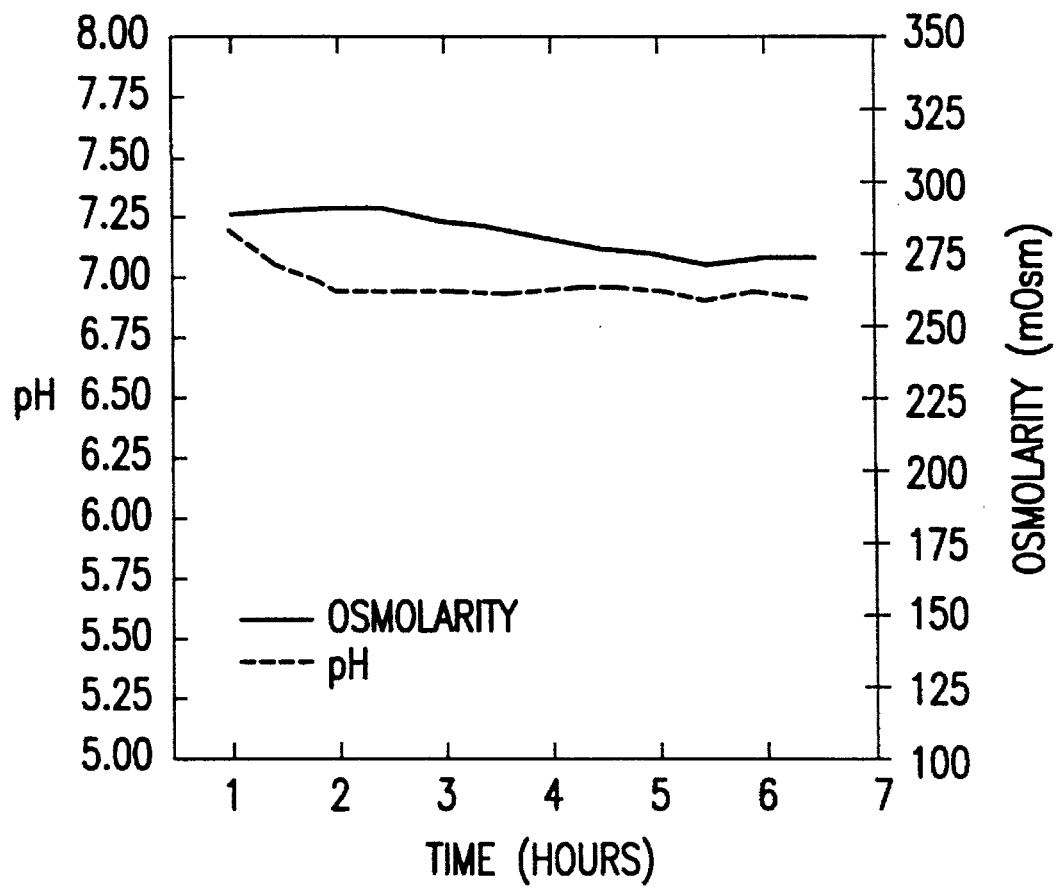
FIG. 2 shows the monitored pH and osmolarity over time of RPMI-1640 media prepared by the continuous admixture of a sufficient amount of concentrated subgroups with a sufficient amount of water to make a 1× media formulation.
Figure 3:
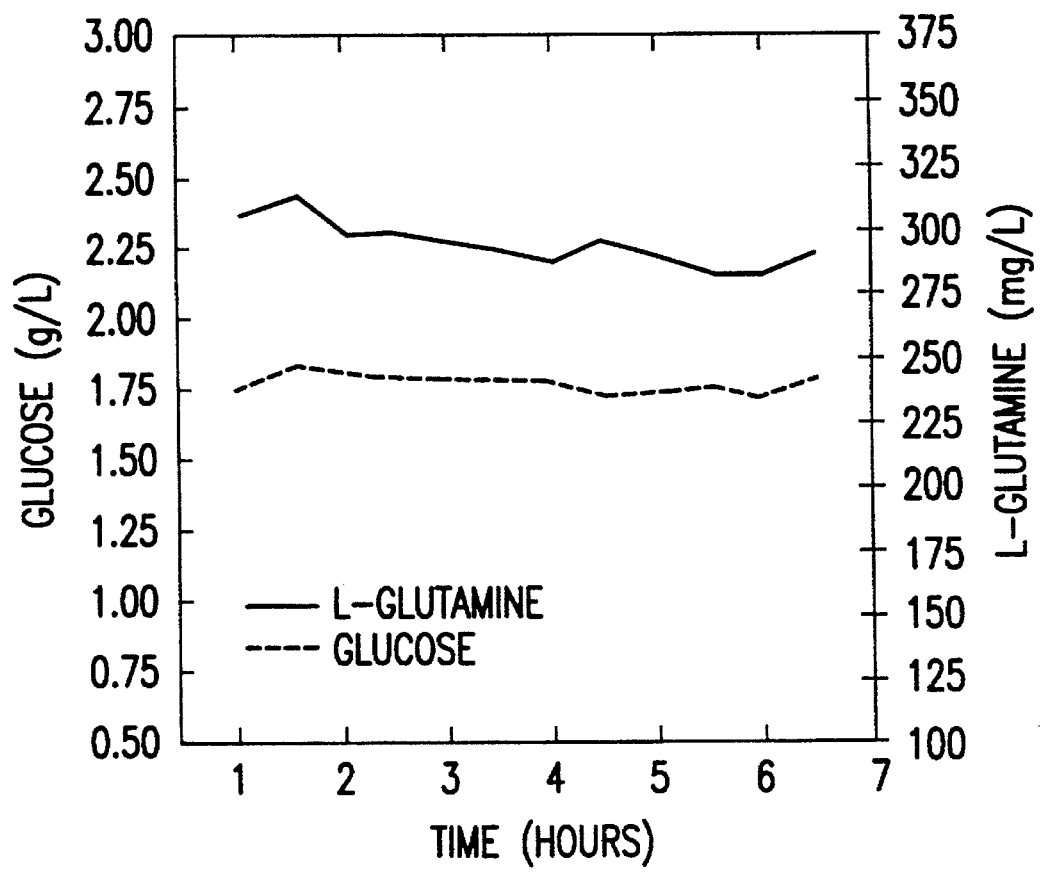
FIG. 3 shows the monitored level of L-glutamine and glucose over time. The samples were taken from a mixing chamber during the continuous admixture of concentrated subgroups with water.
Figure 4:
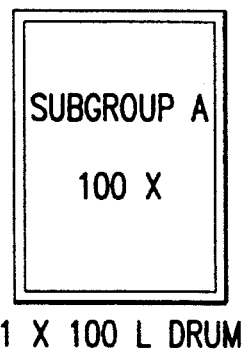
FIG. 4 shows a kit comprising large containers containing concentrated subgroups. The concentrated subgroups may be admixed and diluted to give a total of 10,000 liters of media.
Figure 4:
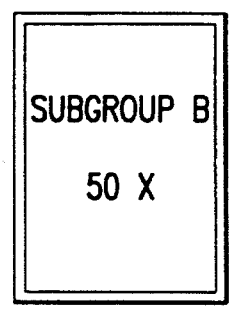
Figure 4:
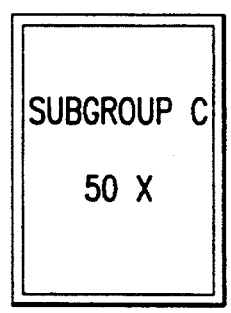

Reconstitution of RPMI-1640 Medium Concentrated Subgroups Using a Continuous Feed Mixing Chamber A reconstitution experiment was carried out using RPMI-1640 media concentrate subgroups in the 15 L Biospin bioreactor. Three media subgroups at 50× per subgroup and two 25× $NaHCO_3$ subgroup were continually pumped into the bioreactor at a rate of 250 ml/hour. Deionized distilled water was pumped into the reactor at a rate of 12.5 L per hour. The perfused concentrates were continually admixed in the mixing chamber. Complete 1× medium formulation was removed from the Biospin bioreactor at a rate of 12.5 L per hour. The pH of the medium was monitored both internally and externally. Medium parameters (pH, osmolarity, amino acids, glucose, glutamine) were measured throughout the perfusion. The results of the study indicate that RPMI-1640 concentrated subgroups can be reconstituted in the Biospin bioreactor and the resulting 1× medium formulation parameters show significant correlation with the RPMI-1640 formulation (FIGS. 2,3 and Table 5).

TABLE 5

Concentrate Reconstitution of RPMI 1640 Trial 1 HPLC Assay Results

| Amino Acid | Medium Theo. | Conc. Std | Hour 1 | Hour 3 | Hour 5 | Hour 6.5 |
|---|---|---|---|---|---|---|
| Aspartate | 20.00 | 20.30 | 21.00 | 20.93 | 20.77 | 19.47 |
| Glutamate | 20.00 | 20.84 | 23.91 | 22.46 | 21.05 | 19.95 |
| Hydroxy-proline | 20.00 | 25.92 | 24.98 | 26.93 | 25.39 | 24.61 |
| Asparginine | 50.00 | 41.60 | 44.84 | 45.96 | 45.70 | 44.34 |
| Arginine | 200.00 | 192.03 | 199.53 | 197.26 | 198.54 | 195.83 |
| Threonine | 20.00 | 33.04 | 40.01 | 34.91 | 35.63 | 30.51 |
| Proline | 20.00 | 32.78 | 36.93 | 31.11 | 32.05 | 32.34 |
| Tyrosine | 20.00 | 25.84 | 26.63 | 26.77 | 24.81 | 19.11 |
| Valine | 20.00 | 22.15 | 22.90 | 22.66 | 21.83 | 18.40 |
| Methionine | 15.00 | 16.12 | 17.18 | 18.06 | 17.70 | 14.00 |
| Cysteine | 50.00 | 35.64 | 39.51 | 39.09 | 43.04 | 34.86 |
| Isoleucine | 50.00 | 56.71 | 53.72 | 51.85 | 51.38 | 49.54 |
| Leucine | 50.00 | 54.04 | 52.97 | 52.40 | 50.74 | 50.25 |
| Phenylalanine | 15.00 | 16.59 | 19.76 | 18.88 | 19.61 | 17.73 |
| Tryptophan | 5.00 | 4.66 | 7.67 | 7.62 | 7.99 | 6.47 |
| Lysine | 40.00 | 28.41 | 32.37 | 29.00 | 32.87 | 30.05 |
| Histidine | 15.000 | 15.000 | 14.414 | 13.899 | 12.884 | 10.540 |
| Serine | 30.000 | 30.000 | 31.030 | 30.399 | 30.745 | 22.250 |
| Glycine | 10.000 | 10.000 | 11.495 | 13.588 | 12.677 | 9.172 |

EXAMPLE IV

Preparation of DMEM Media

DMEM media (Dulbecco's Modified Eagle's Medium (GIBCO/BRL Catalogue and Reference Guide, pg. 96, 1990; Dulbecco, R. et al. *Virology* 8:396 (1959); and Smith, J. D. et al. *Virology* 12:185 (1960) was prepared by dividing the ingredients of this media into an acid-soluble subgroup, a glutamine-containing subgroup and a weak acid-base soluble subgroup. The ingredients of DMEM media were divided and prepared as a concentrated subgroups as shown in Tables 6, 7, 8 and 9. A procedure similar to that described in Example II was used.

Table 9 also shows the procedure used for mixing and diluting the DMEM subgroups to make a 1× formulation of DMEM. NaOH was added to the 1× media to adjust the final pH to 7.3. NaHCO$_3$ was added as a buffering agent.

TABLE 6

Acid Soluble Subgroup for DMEM Media

| Components | MW | g/L | μM |
|---|---|---|---|
| L-Arginine.HCl | 210.66 | 0.084 | 398.7 |

TABLE 6-continued

Acid Soluble Subgroup for DMEM Media

| Components | MW | g/L | μM |
|---|---|---|---|
| L-Cystine.2HCL | 313.22 | 0.06257 | 199.8 |
| L-Glycine | 75.0 | 0.030 | 400.0 |
| L-Histidine.HCl.H$_2$O | 209.46 | 0.042 | 200.5 |
| L-Isoleucine | 131.0 | 0.105 | 801.5 |
| L-Leucine | 131.0 | 0.105 | 801.5 |
| L-Lysine.HCl | 182.46 | 0.146 | 800.2 |
| L-Methionine | 149.0 | 0.030 | 201.3 |
| L-Phenylalanine | 165.0 | 0.066 | 400.0 |
| L-Serine | 105.0 | 0.042 | 400.0 |
| L-Threonine | 119.0 | 0.095 | 798.3 |
| L-Tryptophan | 204.0 | 0.016 | 78.4 |
| L-Tyrosine | 181.0 | 0.072 | 397.8 |
| L-Valine | 117.0 | 0.094 | 803.4 |
| NaH$_2$PO$_4$.H$_2$O | 137.98 | 0.125 | 905.9 |
| Thiamine.HCl | 337.28 | 0.004 | 11.9 |
| FeCl3.6H$_2$O | 270.22 | 0.000054 | 0.2 |

TABLE 7

Glutamine-Containing Subgroup for DMEM Media

| Components | MW | g/L | μM |
|---|---|---|---|
| CaCl$_2$ (anhyd) | 110.99 | 0.200 | 1802.0 |
| NaCl | 58.45 | 5.400 | 92386.7 |
| MgCl2 (anhyd) | 95.23 | 0.07726 | 811.3 |
| D—Ca Pantothenate | 476.53 | 0.004 | 8.4 |
| L-Glutamine | 146.15 | 0.584 | 3995.9 |

TABLE 8

Weak Acid-Base Soluble Solution for DMEM Media

| Components | MW | g/L | μM |
|---|---|---|---|
| NaCl | 58.45 | 0.400 | 6843.5 |
| Glucose | 180.16 | 4.500 | 24977.8 |
| Na-Pyruvate | 111.05 | 0.110 | 990.5 |
| Choline Chloride | 140.0 | 0.004 | 28.6 |
| Folic Acid | 441.0 | 0.004 | 9.1 |
| Inositol | 180.0 | 0.0072 | 40.0 |
| Niacinamide | 122.0 | 0.004 | 32.8 |
| Pyridoxal.HCl | 203.62 | 0.004 | 19.6 |
| Riboflavin | 376.0 | 0.0004 | 1.1 |
| KCl | 74.56 | 0.400 | 5364.8 |

TABLE 9

Procedure for Preparation of DMEM Subgroups

1. DMEM High Glucose
  Glutamine-Containing subgroup
  18.1 ml H2O
  6.3 g DPM 20.0 ml Total Volume  pH 5.50  5 0 X
  Concentrate
2. DMEM High Glucose
  Weak Acid-Base Soluble Subgroup
  17.0 ml H2O
  5.4 g DPM
  0.7 ml 0.1N NAOH 20.0 ml Total Volume  pH 6.60  5 0 X
  Concentrate
3. DMEM High Glucose
  Acid Soluble Subgroup

TABLE 9-continued 18.5 ml H2O
1.1 g DPM
1.5 ml 5N HCl 20.0 ml Total Volume    pH 0.80    50 X Concentrate Procedure for Preparing a 1× DMEM Media Formulation 900.0 ml H2O
 20.0 ml Glutamine-Containing Subgroup
 20.0 ml Weak Acid-Base Subgroup
 20.0 ml Acid Soluble Subgroup
 3.7 g NaHCO3
ADD 5N NaOH to bring pH to 7.30
ADD H2O to bring volume to 1000.0 ml 1000.0 ml Total Volume    pH 7.30    1× Formulation
Osmolarity will be 315–340 mOsm. Osmolarity will change with the amount of acid/base used for the solubilization of components in each subgroup. If the osmolarity falls above the desired limits an adjustment in the NaCl concentration can be made to lower the osmolarity.

EXAMPLE V

Preparation of HAM's F-12 Medium

HAM's F-12 medium (Ham, R. G., *Proc. Natl. Acad. Sci.* 53:288 (1965)) is prepared by dividing the ingredients of this media into an acid-soluble subgroup, a glutamine-containing subgroup, and a weak acid/base subgroup. The compositions of the respective subgroups are set out in Tables 10, 11 and 12. A procedure similar to that described in Example II may be used to prepare the media concentrates.

TABLE 10

ACID SOLUBLE SUBGROUP FOR HAM'S F-12 MEDIUM

| COMPONENT | mg/L |
| --- | --- |
| L-ALANINE | 8.90 |
| L-ARGININE.HCL | 211.00 |
| L-ASPARAGINE.H$_2$O | 15.01 |
| L-ASPARTIC ACID | 13.30 |
| L-CYSTEINE.HCL.H$_2$O | 35.12 |
| L-GLUTAMIC ACID | 14.70 |
| GLYCINE | 7.50 |
| L-HISTIDINE.HCL.H$_2$O | 20.96 |
| L-ISOLEUCINE | 3.94 |
| L-LEUCINE | 13.10 |
| L-LYSINE.HCL | 36.50 |
| L-METHIONINE | 4.48 |
| L-PHENYLALANINE | 4.96 |
| L-PROLINE | 34.50 |
| L-SERINE | 10.50 |
| L-THREONINE | 11.90 |
| L-TRYPTHPHAN | 2.04 |
| L-TYROSINE | 5.40 |
| L-VALINE | 11.70 |
| THIAMINE.HCL | 0.34 |
| FeSO$_4$.7H$_2$O | 0.834 |

TABLE 11

GLUTAMINE CONTAINING SUBGROUP FROM HAM'S F-12 MEDIUM

| COMPONENT | mg/L |
| --- | --- |
| L-GLUTAMINE | 146.00 |
| D—CA PANTOTHENATE | 0.48 |
| CaCl$_2$ (anhyd) | 33.22 |
| MgCl$_2$ (anhyd) | 57.22 |
| NaCl | 6000.00 |

TABLE 12

WEAK ACID/BASE SUBGROUP FOR HAM'S F-12 MEDIUM

| COMPONENT | mg/L |
| --- | --- |
| BIOTIN | 0.0073 |
| CHOLINE CHLORIDE | 13.9600 |
| FOLIC ACID | 1.3000 |
| i-INOSITOL | 18.0000 |
| NIACINAMIDE | 0.0370 |
| PYRIDOXINE.HCL | 0.0620 |
| RIBOFLAVIN | 0.0380 |
| VITAMIN B$_{12}$ | 1.3600 |
| D-GLUCOSE | 1802.0000 |
| HYPOXANTHINE (sodium salt) | 4.7700 |
| LINOLEIC ACID | 0.0840 |
| LIPOIC ACID | 0.2100 |
| PHENOL RED | 1.2000 |
| PUTRESCINE.2HCL | 0.1610 |
| SODIUM PYRUVATE | 110.0000 |
| THYMIDINE | 0.7300 |
| CUSO$_4$.5H$_2$O | 0.0025 |
| KCL | 223.6000 |
| NaCl | 1599.0000 |
| Na$_2$HPO$_4$ (anhyd) | 142.0400 |
| ZnSO$_4$.7H$_2$O | 0.8630 |

EXAMPLE VI

Preparation of DMEM/F-12 Medium

DMEM/F-12 medium (GIBCO/BRL Catalogue and Reference Guide, page 97 (1990)) is prepared by dividing the ingredients of this media into an acid-soluble subgroup, a glutamine-containing subgroup, and a weak acid/base subgroup. The compositions of the respective subgroups are set out in Tables 13, 14 and 15. A procedure similar to that described in Example II may be used to prepare the media concentrates.

TABLE 13

ACID SOLUBLE SUBGROUP FOR DMEM/F-12 MEDIUM

| COMPONENT | mg/L |
| --- | --- |
| L-ALANINE | 4.45 |
| L-ARGININE.HCL | 147.50 |
| L-ASPARAGINE.H$_2$O | 7.50 |
| L-ASPARTIC ACID | 6.65 |
| L-CYSTEINE.HCL.H$_2$O | 17.56 |
| L-GLUTAMIC ACID | 7.35 |
| GLYCINE | 18.75 |
| L-HISTIDINE.HCL.H$_2$O | 31.48 |
| L-ISOLEUCINE | 54.47 |
| L-LEUCINE | 59.05 |
| L-LYSINE.HCL | 91.25 |
| L-METHIONINE | 17.24 |
| L-PHENYLALANINE | 35.48 |

TABLE 13-continued

ACID SOLUBLE SUBGROUP FOR DMEM/F-12 MEDIUM

| COMPONENT | mg/L |
|---|---|
| L-PROLINE | 17.25 |
| L-SERINE | 26.25 |
| L-THREONINE | 53.45 |
| L-TRYPTOPHAN | 9.02 |
| L-TYROSINE | 38.39 |
| L-VALINE | 52.85 |
| THIAMINE.HCL | 2.17 |
| $FeSO_4.7H_2O$ | 0.417 |
| $NaH_2PO_4.H_2O$ | 42.50 |
| L-CYSTINE.2HCL | 31.29 |
| $Fe(NO_3).9H_2O$ | 0.05 |

TABLE 14

WEAK ACID/BASE SUBGROUP FOR DMEM/F-12 MEDIUM

| COMPONENT | mg/L |
|---|---|
| BIOTIN | 0.0035 |
| CHOLINE CHLORIDE | 8.9800 |
| FOLIC ACID | 2.6500 |
| i-INOSITOL | 12.6000 |
| NIACINAMIDE | 2.0200 |
| PYRIDOXINE.HCL | 0.0310 |
| RIBOFLAVIN | 0.2190 |
| VITAMINE $B_{12}$ | 0.0680 |
| D-GLUCOSE | 3151.0000 |
| HYPOXANTHINE (sodium salt) | 2.3900 |
| LINOLEIC ACID | 0.0420 |
| LIPOIC ACID | 0.1050 |
| PHENOL RED | 8.1000 |
| PUTRESCINE.2HCL | 0.0810 |
| SODIUM PYRUVATE | 55.0000 |
| THYMIDINE | 0.3650 |
| $CuSO_4.5H_2O$ | 0.0013 |
| KCL | 311.8000 |
| NaCL | 999.5000 |
| $Na_2HPO_4$ (anhyd) | 71.02 |
| $ZnSO_4.7H_2O$ | 0.4320 |
| $NaH_2PO_4.H_2O$ | 20.0000 |
| PYRIDOXAL.HCL | 2.0000 |
| HEPES | 3574.5000 |

TABLE 15

GLUTAMINE CONTAINING SUBGROUP FOR DMEM/F-12 MEDIUM

| COMPONENT | mg/L |
|---|---|
| L-GLUTAMINE | 365.00 |
| D—CA PANTOTHENATE | 2.24 |
| $CaCL_2$ (anhyd) | 116.60 |
| $MgCl_2$ (anhyd) | 28.64 |
| $MgSO_4$ | 48.84 |
| NaCl | 6000.00 |

EXAMPLE VII

Preparation of IMDM Medium

IMDM medium (Dulbecco, R. and Freeman, G., *Virology* 8:396 (1959); Smith, J. D. et al., *Virology* 12:185 (1960); Tissue Culture Standards Committee, *In Vitro* 6:2,93; *In Vitro* 9:6 (1970); Iscove, N. N. and Melchers, F., *J. Exp. Med.* 147:923) is prepared by dividing the ingredients of this media into an acid-soluble subgroup, a glutamine-containing subgroup, and a weak acid/base subgroup. The compositions of the respective subgroups are set out in Tables 16, 17 and 18. A procedure similar to that described in Example II may be used to prepare the media concentrates.

TABLE 16

ACID SOLUBLE SUBGROUP FOR IMDM MEDIUM

| COMPONENT | mg/L |
|---|---|
| L-ALANINE | 25.00 |
| L-ARGININE.HCL | 84.00 |
| L-ASPARAGINE.$H_2O$ | 84.00 |
| L-ASPARTIC ACID | 30.00 |
| L-CYSTINE.2HCL | 91.24 |
| L-GLUTAMIC ACID | 75.00 |
| GLYCINE | 30.00 |
| L-HISTIDINE.HCL.$H_2O$ | 42.00 |
| L-ISOLEUCINE | 105.00 |
| L-LEUCINE | 105.00 |
| L-LYSINE.HCL | 146.00 |
| L-METHIONINE | 30.00 |
| L-PHENYLALANINE | 66.00 |
| L-PROLINE | 40.00 |
| L-SERINE | 42.00 |
| L-THREONINE | 95.00 |
| L-TRYPTOPHAN | 16.00 |
| L-TYROSINE | 71.43 |
| L-VALINE | 94.00 |
| THIAMINE.HCL | 4.00 |
| $NaH_2PO_4.H_2O$ | 125.00 |

TABLE 17

WEAK ACID/BASE SUBGROUP FOR IMDM MEDIUM

| COMPONENT | mg/L |
|---|---|
| BIOTIN | 0.0130 |
| CHOLINE CHLORIDE | 4.0000 |
| FOLIC ACID | 4.0000 |
| i-INOSITOL | 7.2000 |
| NIACINAMIDE | 4.0000 |
| PYRIDOXAL.HCL | 4.0000 |
| RIBOFLAVIN | 0.4000 |
| VITAMINE $B_{12}$ | 0.0130 |
| D-GLUCOSE | 4500.000 |
| HEPES | 5958.0000 |
| PHENOL RED | 15.0000 |
| SODIUM PYRUVATE | 110.0000 |
| KCL | 330.0000 |
| $KNO_3$ | 0.0760 |
| $NaSeO_35H_2O$ | 0.0173 |

TABLE 18

GLUTAMINE CONTAINING SUBGROUP FOR IMDM MEDIUM

| COMPONENT | mg/L |
|---|---|
| L-GLUTAMINE | 584.00 |
| D—CA PANTOTHENATE | 4.00 |
| $CaCl_2$ (anhyd) | 165.0 |
| $MgSO_4$ (anhyd) | 97.67 |
| NaCl | 4505.00 |

Modifications of the above-described modes for carrying out the invention that are obvious to persons of skill in the media and fermentation art and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practice within the scope of the appended claims.

What is claimed is:

1. A method of preparing a cell culture medium comprising:
   (a) dividing the ingredients of a cell culture medium into at least the first three, but no more than six, of the following compatible subgroups, said compatible subgroups consisting of:
      i. an acid soluble subgroup consisting essentially of at least one ingredient selected from the group consisting of thiamine, ascorbic acid, a ferric salt, a ferrous salt, guanine, adenine, glutathione, monobasic alkali metal phosphates, and amino acids, or derivatives thereof, other than glutamine;
      ii. a glutamine-containing subgroup consisting essentially of glutamine stabilized with one or more divalent cations selected from the group consisting of calcium and magnesium wherein the ratio of glutamine to divalent cations is in the range of from 2:1 to 2.9:1, and up to two additional ingredients selected from the group consisting of D-Ca pantothenate and sodium chloride;
      iii. a weak acid-base soluble subgroup consisting essentially of at least one ingredient selected from the group consisting of a sugar, a nucleoside, a nucleotide, riboflavin, potassium chloride, sodium chloride, a trace metal, a lipid, an acetate salt, a phosphate nit, HEPES, phenol red, a pyruvate salt, a buffer, and a water soluble vitamin other than thiamine, ascorbic acid, and Ca-pantothenate;
      iv. an alkali soluble subgroup consisting essentially of at least one ingredient selected from the group consisting of purines and pyrimidines that are stable and soluble at an alkaline pH of at least 9.0;
      v. a supplement-containing subgroup consisting essentially of at least one ingredient selected from the group consisting of an antibiotic, serum, yeastolate ultrafiltrate, tryptose phosphate broth, insulin, transferrin, a growth factor, a hormone, albumin, whole egg ultrafiltrate, an attachment factor and sodium bicarbonate; and
      vi. an alcohol soluble subgroup consisting essentially of at least one ingredient selected from the group consisting of cholesterol, a steroid, a fat soluble vitamin, a fatty acid, a lipid, TWEEN 80, or 2-mercaptoethanol;
   b) dissolving each of said subgroups in a liquid carrier to give concentrated solutions of said subgroups greater than 10× in the respective carrier;
   (c) adjusting, if necessary, the pH's of the subgroups so that:
      i. the pH of the acid soluble subgroup is in the range of from about 0 to about 1.0;
      ii. the pH of the glutamine containing subgroup is in the range of from 4.0 to 6.0;
      iii. the pH of the weak acid-base soluble subgroup is in the range of from about 4.0 to 9.0; and
      iv. the pH of the alkali-soluble subgroup is at least about 9.0; and
   (d) admixing a sufficient amount of each of said subgroups obtained in the foregoing steps with a sufficient amount of a diluent to give said cell culture medium.

2. The method of claim 1 wherein the ingredients of the cell culture medium are divided into three compatible subgroups, said compatible subgroups comprising:
   i. an acid soluble subgroup consisting essentially of at least one ingredient selected from the group consisting of thiamine, ascorbic acid, a ferric salt, a ferrous salt, guanine, adenine, glutathione, monobasic alkali metal phosphates, and amino acids, or derivatives thereof, other than glutamine;
   ii. a glutamine-containing subgroup consisting essentially of glutamine stabilized with one or more divalent cations selected from the group consisting of calcium and magnesium wherein the ratio of glutamine to divalent cations is in the range of from 2:1 to 2.9:1, and up to two additional ingredients selected from the group consisting of D-Ca pantothenate and sodium chloride; and
   iii. a weak acid-base soluble subgroup consisting essentially of at least one ingredient selected from the group consisting of a sugar, a nucleoside, a nucleotide, riboflavin, potassium chloride, sodium chloride, a trace metal, a lipid, an acetate salt, a phosphate salt, HEPES, phenol red, a pyruvate salt, a buffer, and a water soluble vitamin other than thiamine, ascorbic acid, and Ca-pantothenate.

3. The method of claim 1 wherein the ingredients of the cell culture medium are divided into four compatible subgroups, said compatible subgroups comprising:
   i. an acid soluble subgroup consisting essentially of at least one ingredient selected from the group consisting of thiamine, ascorbic acid, a ferric salt, a ferrous salt, guanine, adenine, glutathione, monobasic alkali metal phosphates, and amino acids, or derivatives thereof, other than glutamine;
   ii. a glutamine-containing subgroup consisting essentially of glutamine stabilized with one or more divalent cations selected from the group consisting of calcium and magnesium wherein the ratio of glutamine to divalent cations is in the range of from 2:1 to 2.9:1, and up to two additional ingredients selected from the group consisting of D-Ca pantothenate and sodium chloride;
   iii. a weak acid-base soluble subgroup consisting essentially of at least one ingredient selected from the group consisting of a sugar, a nucleoside, a nucleotide, riboflavin, potassium chloride, sodium chloride, a trace metal, a lipid, an acetate salt, a phosphate salt, HEPES, phenol red, sodium pyruvate, a buffer, and a water soluble vitamin other than thiamine, ascorbic acid, and Ca-pantothenate; and
   iv. sodium bicarbonate.

4. The method of claim 1, wherein the cell culture medium is a 10× media formulation.

5. The method of claim 1, wherein the cell culture medium is a 1× media formulation.

6. The method of claim 1, wherein the cell culture medium is a RPMI-1640 medium.

7. The method of claim 1, wherein the cell culture medium is a DMEM medium.

8. The method of claim 1, wherein the cell culture medium is a HAM's F-12 medium.

9. The method of claim 1, wherein said admixing is accomplished in a batch system.

10. The method of claim 1, wherein said admixing is accomplished in a continuous system.

11. The method of claim 1, wherein the concentrated solution obtained in step (b) is about 25×.

12. The method of claim 1, wherein the concentrated solution obtained in step (b) is about 50×.

13. The method of claim 1, wherein the concentrated solution obtained in step (b) is about 100×.

14. A method for preparing a cell culture medium, comprising admixing a sufficient amount of an aqueous diluent with sufficient amounts of at least three, but no more than six, subgroups of ingredients dissolved in a liquid carrier, at least one of said subgroups being in a greater than 10× concentration, said subgroups consisting of:

i. an acid soluble subgroup consisting essentially of at least one ingredient selected from the group consisting of thiamine, ascorbic acid, a ferric salt, a ferrous salt, guanine, adenine, glutathione, monobasic alkali metal phosphates, and amino acids, or derivatives thereof, other than glutamine and having a pH in the range of from about 0 to about 1.0 when dissolved in said liquid carrier;

ii. a glutamine-containing subgroup consisting essentially of glutamine stabilized with one or more divalent cations selected from the group consisting of calcium and magnesium wherein the ratio of glutamine to divalent cations is in the range of from 2:1 to 2.9:1, and up to two additional ingredients selected from the group consisting of D-Ca pantothenate and sodium chloride and having a pH in the range of from 4.0 to 6.0 when dissolved in said liquid carrier;

iii. a weak acid-base soluble subgroup consisting essentially of at least one ingredient selected from the group consisting of a sugar, a nucleoside, a nucleotide, riboflavin, potassium chloride, sodium chloride, a trace metal, a lipid, an acetate salt, a phosphate salt, HEPES, phenol red, a pyruvate salt, a buffer, and a water soluble vitamin other than thiamine, ascorbic acid, and Ca-pantothenate and having a pH in the range of from 4.0 to 9.0 when dissolved in said liquid carrier, iv. an alkali soluble subgroup consisting essentially of at least one ingredient selected from the group consisting of purines and pyrimidines having no loss of stability or solubility when dissolved in said liquid carrier at an alkaline pH of at least about 9.0;

v. a supplement-containing subgroup consisting essentially of at least one ingredient selected from the group consisting of an antibiotic, serum, yeastolate ultrafiltrate, tryptose phosphate broth, insulin, transferrin, a growth factor, a hormone, albumin, whole egg ultrafiltrate, an attachment factor and sodium bicarbonate; and vi. an alcohol soluble subgroup consisting essentially of at least one ingredient selected from the group consisting of cholesterol, a steroid, a fat soluble vitamin, a fatty acid, a lipid, TWEEN 80, or 2-mercaptoethanol; to give said cell culture medium.

15. The method of claim 14, wherein said admixing is accomplished in a batch system.

16. The method of claim 14, wherein said admixing is accomplished in a continuous system.

17. A method of preparing an RPMI-1640 medium comprising:

(a) dividing the ingredients of the RPMI-1640 medium into subgroups, said subgroups consisting of:

i. an acid soluble subgroup consisting essentially of L-arginine, L-asparagine, L-aspartic acid, L-cystine.2HCl, L-glutamic acid, glycine, L-histidine, L-hydroxyproline, L-isoleucine, L-leucine, L-lysine-.HCl, L-methionine, L-phenylalanine, L-proline, L-serine, L-threonine, L-tryptophan, L-tyrosine, L-valine, and thiamine.HCl, ii. a glutamine-containing subgroup consisting essentially of glutamine, calcium nitrate, magnesium chloride, sodium chloride, and calcium pantothenate, iii. a weak acid-base soluble subgroup consisting essentially of biotin, choline chloride, folic acid, i-inositol, niacinamide, para-aminobenzoic acid, pyridoxine, riboflavin, vitamin B12, glucose, glutathione, phenol red, disodium hydrogen phosphate, and potassium chloride, and iv. sodium bicarbonate;

(b) dissolving each of the subgroups of compatible ingredients in a liquid carrier to give concentrated solutions of the subgroups greater than 10× in the respective carrier;

(c) adjusting, if necessary, the pH's of the subgroups so that:

i. the pH of the acid soluble subgroup is in the range of from about 0 to about 1.0;

ii. the pH of the glutamine containing subgroup is in the range of from 4.0 to 6.0;

iii. the pH of the weak acid-base soluble subgroup is in the range of from about 4.0 to 9.0 and (d) admixing a sufficient amount of each of the subgroups obtained in step (b) with a sufficient amount of a diluent to produce the RPMI-1640 media.

18. A method of preparing a DMEM medium comprising:

(a) dividing the ingredients of the DMEM medium into subgroups, said subgroups consisting of:

i. an acid soluble subgroup consisting essentially of thiamine, sodium dihydrogen phosphate, ferric chloride, L-arginine, L-cystine.2HCl, glycine, L-histidine, L-isoleucine, L-leucine, L-lysine.HCl, L-methionine, L-phenylalanine, L-serine, L-threonine, L-tryptophan, L-tyrosine, and L-valine, ii. a glutamine-containing subgroup consisting essentially of glutamine, calcium chloride, sodium chloride, magnesium chloride, and calcium pantothenate, iii. a weak acid-base soluble subgroup comprising glucose, potassium chloride, sodium chloride, sodium pyruvate, choline chloride, folic acid, inositol, niacinamide, pyridoxal, and riboflavin, and iv. sodium bicarbonate;

(b) dissolving each of the subgroups of compatible ingredients in a liquid carrier to give concentrated solutions of the subgroups greater than 10× in the respective carrier;

(c) adjusting, if necessary, the pH's of the subgroups so that:

i. the pH of the acid soluble subgroup is in the range of from about 0 to about 1.0;

ii. the pH of the glutamine containing subgroup is in the range of from 4.0 to 6.0;

iii. the pH of the weak acid-base soluble subgroup is in the range of from about 4.0 to 9.0; and (d) admixing a sufficient amount of each of the subgroups obtained in step (b) with a sufficient amount of a diluent to produce the DMEM media.

19. A method of preparing a HAM's F-12 medium comprising:

(a) dividing the ingredients of the HAM's F-12 medium into subgroups, said subgroups consisting of:

i. an acid soluble subgroup consisting essentially of thiamine, ferrous sulfate, L-alanine, L-arginine, L-asparagine, L-aspartic acid, L-cysteine.HCl.H₂O, L-glutamic acid, glycine, L-histidine, L-isoleucine, L-leucine, L-lysine.HCl, L-methionine, L-phenylalanine, L-proline, L-serine, L-threonine, L-tryptophan, L-tyrosine, and L-valine;

ii a glutamine-containing subgroup consisting essentially of glutamine, calcium chloride, sodium chloride, magnesium chloride, and calcium pantothenate, and iii. a weak acid-base soluble subgroup consisting essentially of glucose, potassium chloride, sodium chloride, sodium pyruvate, choline chloride, folic acid, i-inositol, niacinamide, pyridoxine, biotin, vitamin B12, hypoxanthine, linoleic acid, lipoic acid, phenol red, putrescine, thymidine, copper sulfate, disodium hydrogen phosphate, zinc sulfate, and riboflavin;

(b) dissolving each of the subgroups of compatible ingredients in a liquid carrier to give concentrated solutions of the subgroups greater than 10× in the respective carrier;

(c) adjusting, if necessary, the pH's of the subgroups so that:
   i. the pH of the acid soluble subgroup is in the range of from about 0 to about 1.0;
   ii. the pH of the glutamine containing subgroup is in the range of from 4.0 to 6.0;
   iii. the pH of the weak acid-base subgroup is in the range of from about 4.0 to 9.0; and (d) admixing a sufficient amount of each of the subgroups obtained in step (b) with a sufficient amount of a diluent to produce the HAM's F-12 medium.

20. A kit for making a cell culture medium, wherein said kit comprises a carrier being compartmentalized to receive in close confinement from one to six container means wherein:

(a) a first container means contains a solution of compatible ingredients of an acid soluble subgroup consisting essentially of at least one ingredient selected from the group consisting of thiamine, ascorbic acid, a ferric salt, a ferrous salt, guanine, adenine, glutathione, monobasic alkali metal phosphates, and amino acids, or derivatives thereof, other than glutamine;

(b) a second container means contains a solution of compatible ingredients of a glutamine-containing subgroup consisting essentially of glutamine stabilized with one or more divalent cations selected from the group consisting of calcium and magnesium wherein the ratio of glutamine to divalent cations is in the range of from 2:1 to 2.9:1, and up to two additional ingredients selected from the group consisting of D-Ca pantothenate and sodium chloride;

(c) a third container means contains a solution of compatible ingredients of a weak acid-base soluble subgroup consisting essentially of at least one ingredient selected from the group consisting of a sugar, a nucleoside, a nucleotide, riboflavin, potassium chloride, sodium chloride, a trace metal, a lipid, an acetate salt, a phosphate salt, HEPES, phenol red, a pyruvate salt, a buffer, and a water soluble vitamin other than thiamine, ascorbic acid, and Ca-pantothenate;

(d) a fourth container means contains a solution of compatible ingredients of a supplement-containing subgroup consisting essentially of at least one ingredient selected from the group consisting of an antibiotic, serum, yeastolate ultrafiltrate, tryptose phosphate broth, insulin, transferrin, a growth factor, a hormone, albumin, whole egg ultrafiltrate, an attachment factor and sodium bicarbonate;

(e) a fifth container means contains a solution of compatible ingredients of an alcohol soluble subgroup consisting essentially of at least one ingredient selected from the group consisting of cholesterol, a steroid, a fat soluble vitamin, a fatty acid, a lipid, a menadione, TWEEN 80, or 2-mercaptoethanol, (f) a sixth container means contains a solution of compatible ingredients of an alkali soluble subgroup consisting essentially of at least one ingredient selected from the group consisting of purines and pyrimidines that are stable and soluble at an alkaline pH of at least 9.0;

wherein said solution of compatible ingredients in at least one of said container means is a concentrated solution greater than 10×; and with the proviso that said second container means must be present.

21. The kit of claim 20, wherein the cell culture medium is a RPMI-1640 medium.

22. The kit of claim 20, wherein the cell culture medium is a DMEM medium.

23. The kit of claim 20, wherein the cell culture medium is a HAM's F-12 medium.

24. The kit of claim 20, wherein said concentrated solution is about 25×.

25. The kit of claim 20, wherein said concentrated solution is about 50×.

26. The kit of claim 20, wherein said concentrated solution is sterile.

27. A kit for making RPMI-1640 medium, wherein said kit comprises a carrier being compartmentalized to receive in close confinement therein:

(a) a first container means containing a solution of compatible ingredients of an acid soluble subgroup consisting essentially of L-arginine, L-asparagine, L-aspartic acid, L-cystine.2HCl, L-glutamic acid, glycine, L-histidine, L-hydroxyproline, L-isoleucine, L-leucine, L-lysine.HCl, L-methionine, L-phenylalanine, L-proline, L-serine, L-threonine, L-tryptophan, L-tyrosine, L-valine, and thiamine.HCl at a pH in the range of from about 0 to about 1.0;

(b) a second container means containing a solution of compatible ingredients of a weak acid-alkali soluble subgroup consisting essentially of biotin, choline chloride, folic acid, i-inositol, niacinamide, para-aminobenzoic acid, pyridoxine, riboflavin, vitamin B12, glucose, glutathione, phenol red, disodium hydrogen phosphate, and potassium chloride at a pH in the range of from about 4.0 to 9.0;

(c) a third container means containing a solution of compatible ingredients of a glutamine-containing subgroup consisting essentially of glutamine, calcium nitrate, magnesium chloride, sodium chloride, and calcium pantothenate at a pH in the range of from 4.0 to 6.0; and (d) a solution of sodium bicarbonate; wherein said solution of compatible ingredients in at least one of said container means is a concentrated solution greater than 10×.

28. A kit for making a DMEM medium, wherein said kit comprises a carrier being compartmentalized to receive in close confinement therein:

(a) a first container means containing a solution of compatible ingredients of an acid soluble subgroup consisting essentially of thiamine, sodium dihydrogen phosphate, ferric chloride, L-arginine, L-cystine.2HCl, glycine, L-histidine, L-isoleucine, L-leucine, L-lysine-.HCl, L-methionine, L-phenylalanine, L-serine, L-threonine, L-tryptophan, L-tyrosine, and L-valine at a pH in the range of from about 0 to about 1.0;

(b) a second container means containing a solution of compatible ingredients of a weak acid-base soluble subgroup consisting essentially of glucose, potassium chloride, sodium chloride, sodium pyruvate, choline chloride, folic acid, inositol, niacinamide, pyridoxal, and riboflavin at a pH in the range of from about 4.0 to 9.0;

(c) a third container means containing a solution of compatible ingredients of a glutamine-containing subgroup comprising glutamine, calcium chloride, sodium chloride, magnesium chloride, and calcium pantothenate at a pH in the range of from 4.0 to 6.0; and (d) a fourth container means containing a solution of sodium bicarbonate; wherein said solution of compatible ingredients in at least one of said container means is a concentrated solution greater than 10×.

29. A kit for making a HAM's F-12 medium, wherein said kit comprises a carrier being compartmentalized to receive in close confinement therein:

(a) a first container means containing a solution of compatible ingredients of an acid soluble subgroup consisting essentially of thiamine, ferrous sulfate, L-alanine, L-arginine, L-asparagine, L-aspartic acid, L-cysteine.HCl.H$_2$O, L-glutamic acid, glycine, L-histidine, L-isoleucine, L-leucine, L-lysine.HCl, L-methionine, L-phenylalanine, L-proline, L-serine, L-threonine, L-tryptophan, L-tyrosine, and L-valine at a pH in the range of from about 0 to about 1.0;

(b) a second container means containing a solution of compatible ingredients of a weak acid-base soluble subgroup consisting essentially of glucose, potassium chloride, sodium chloride, sodium pyruvate, choline chloride, folic acid, i-inositol, niacinamide, pyridoxine, biotin, vitamin B12, hypoxanthine, linoleic acid, lipoic acid, phenol red, putrescine, thymidine, copper sulfate, disodium hydrogen phosphate, zinc sulfate, and riboflavin at a pH in the range of from about 4.0 to 9.0; and (c) a third container means containing a solution of compatible ingredients of a glutamine-containing subgroup consisting essentially of glutamine, calcium chloride, sodium chloride, magnesium chloride, and calcium pantothenate at a pH in the range of from 4.0 to 6.0;

wherein said solution of compatible ingredients in at least one of said container means is a concentrated solution greater than 10×.

* * * * *